(12) United States Patent
Nemoto et al.

(10) Patent No.: US 9,301,813 B2
(45) Date of Patent: Apr. 5, 2016

(54) MEDICAL SUPPORT APPARATUS AND OPERATION METHOD OF MEDICAL SUPPORT APPARATUS

(71) Applicant: Olympus Corporation, Tokyo (JP)

(72) Inventors: Iori Nemoto, Tokyo (JP); Kiyoshi Sekiguchi, Tokyo (JP); Kenji Noda, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/569,222

(22) Filed: Dec. 12, 2014

(65) Prior Publication Data

US 2015/0164611 A1   Jun. 18, 2015

Related U.S. Application Data

(63) Continuation of application No. PCT/JP2014/062062, filed on May 1, 2014.

(30) Foreign Application Priority Data

Jun. 5, 2013   (JP) ................................. 2013-119151

(51) Int. Cl.
   *G06F 17/30*   (2006.01)
   *A61B 19/00*   (2006.01)
(52) U.S. Cl.
   CPC .......... *A61B 19/56* (2013.01); *G06F 17/30705* (2013.01); *A61B 2019/564* (2013.01); *A61B 2019/566* (2013.01)
(58) Field of Classification Search
   None
   See application file for complete search history.

(56) References Cited

U.S. PATENT DOCUMENTS

2003/0190145 A1* 10/2003 Copperman ...... G06F 17/30017
                                                      386/241
2004/0204627 A1* 10/2004 Furukawa .......... A61B 1/00055
                                                      600/118

(Continued)

FOREIGN PATENT DOCUMENTS

JP   A-2003-190084   7/2003
JP   A-2004-105533   4/2004

(Continued)

OTHER PUBLICATIONS

International Search Report issued in International Patent Application No. PCT/JP2014/062062 dated Jul. 15, 2014.

*Primary Examiner* — Syed Hasan
(74) *Attorney, Agent, or Firm* — Oliff PLC

(57) ABSTRACT

A system controller determines whether a difference of recording times of two pieces of operation log data adjacent in time sequence has a time interval equal to or longer than a predetermined time period with respect to the operation log data including identification information, operation contents for respective apparatuses that are used at a time of the surgical operation, and a recording time, and when it is determined that the difference of the recording times of the two pieces of operation log data adjacent in time sequence has a time interval equal to or longer than a predetermined time period, the system controller groups a plurality of operation log data that continue in time sequence, with a difference of the recording times of the two pieces of operation log data adjacent in time sequence being shorter than the predetermined time period, as one scene.

15 Claims, 12 Drawing Sheets

(56) References Cited

U.S. PATENT DOCUMENTS

| | | | | |
|---|---|---|---|---|
| 2007/0016441 A1* | 1/2007 | Stroup | ............ | G06Q 50/22 705/2 |
| 2007/0192133 A1* | 8/2007 | Morgan | ............ | G06F 19/321 705/2 |
| 2009/0326336 A1* | 12/2009 | Lemke | ............ | G06F 19/3437 600/300 |
| 2013/0173282 A1* | 7/2013 | Tee | ............ | G06F 19/3443 705/2 |
| 2013/0268290 A1* | 10/2013 | Jackson | ............ | G06F 19/28 705/2 |

FOREIGN PATENT DOCUMENTS

| | | |
|---|---|---|
| JP | A-2005-065721 | 3/2005 |
| JP | A-2006-252286 | 9/2006 |
| JP | A-2006-263329 | 10/2006 |

\* cited by examiner

FIG. 6

| SCENE | SHADOWLESS LAMP 1 | SHADOWLESS LAMP 2 | INDOOR LIGHT | PNEUMOPERITONEUM APPARATUS | CO2 FEEDING | LIGHT SOURCE APPARATUS 1 (LAPAROSCOPE) | LIGHT SOURCE APPARATUS 2 (ENDOSCOPE) | MONITOR 1 | MONITOR 2 | ESU (LAPAROSCOPE SIDE) | ESU (ENDOSCOPE SIDE) |
|---|---|---|---|---|---|---|---|---|---|---|---|
| 1. PREPARATION | ON | ON | ON | 12mmHg | OFF | Standby | Standby | Laparo | Laparo | 40W | 30W |
| 2. LAPAROSCOPY | OFF | Dark | OFF | Start 15mmHg | → | ON Center | → | → | → | → | → |
| 3. INTRAOPERATIVE ENDOSCOPY | → | → | → | 10mmHg | ON | ON Dark | ON Center | PIP(L&E) | PIP(L&E) | → | → |
| 4. LAPAROSCOPY | → | → | OFF | 15mmHg | OFF | ON Center | Standby | Laparo | Laparo | → | → |
| 5. INTRAOPERATIVE ENDOSCOPY | → | → | → | 10mmHg | ON | ON Dark | ON Center | PIP(L&E) | PIP(L&E) | → | → |
| 6. CLOSE | ON | ON | ON | OFF | OFF | Standby | Standby | PIP(L&E) | OR Camera | → | → |

TBL1

| SCENE | TELECONFERENCE | DESTINATION ADDRESS |
|---|---|---|
| 1 | ON | 00112233 |
| 2 | OFF | — |
| 3 | OFF | — |
| 4 | ON | 44556677 |

FIG. 10

TBL2

| SCENE | CHECKLIST |
|---|---|
| 1 | ABC01 |
| 2 | ABC02 |
| 3 | ABC03 |
| 4 | ABC04 |

FIG. 11

| | |
|---|---|
| ☐ | Has the patient confirmed his/her identity, site, procedure, and consent? |
| ☐ | Is the site marked? |
| ☐ | Is the anaesthrsla machine and medication check complete? |
| ☐ | Is the pulse oxmeter on the patient and functioning? |

FIG. 12

| | |
|---|---|
| ☐ | The name of the procedure |
| ☐ | Completion of instrument,sponge and needle counts |
| ☐ | Specimen labeling (read specimen labels aloud including patient name) |
| ☐ | Whether there are any equipment problems to be addressed |

FIG. 13

DDA

| TIME | LOGON ID | SURGICAL OPERATION NAME | APPARATUS NAME | FUNCTION NAME | CHANGED VALUE |
|---|---|---|---|---|---|
| . . . | . . . | . . . | . . . | . . . | . . . |
| 2013/2/1 09:00:30 | 3 | DEF | Light Source | Standby | ON |
| 2013/2/1 09:00:40 | 3 | DEF | Monitor 1 | Input | A |
| 2013/2/1 09:01:00 | 3 | DEF | Light 1 | ON/OFF | OFF |
| 2013/2/1 10:00:15 | 1 | ABC | Light 1 | ON/OFF | ON |
| 2013/2/1 10:00:20 | 1 | ABC | Light 2 | ON/OFF | ON |
| 2013/2/1 10:00:30 | 1 | ABC | Light Source | Standby | ON |
| 2013/2/1 10:00:40 | 1 | ABC | Monitor 1 | Input | A |
| 2013/2/1 10:00:50 | 1 | ABC | Monitor 2 | Input | A |
| 2013/2/1 10:01:20 | 1 | ABC | Insuflator | Pressure | 12 |
| 2013/2/1 10:01:40 | 1 | ABC | Light 1 | ON/OFF | OFF |
| 2013/2/1 10:01:45 | 1 | ABC | Light 2 | Intensity | 1 |
| 2013/2/1 10:12:00 | 1 | ABC | Insuflator | Start/Stop | Start |
| 2013/2/1 10:12:10 | 1 | ABC | Insuflator | Pressure | 15 |
| . . . | . . . | . . . | . . . | . . . | . . . |

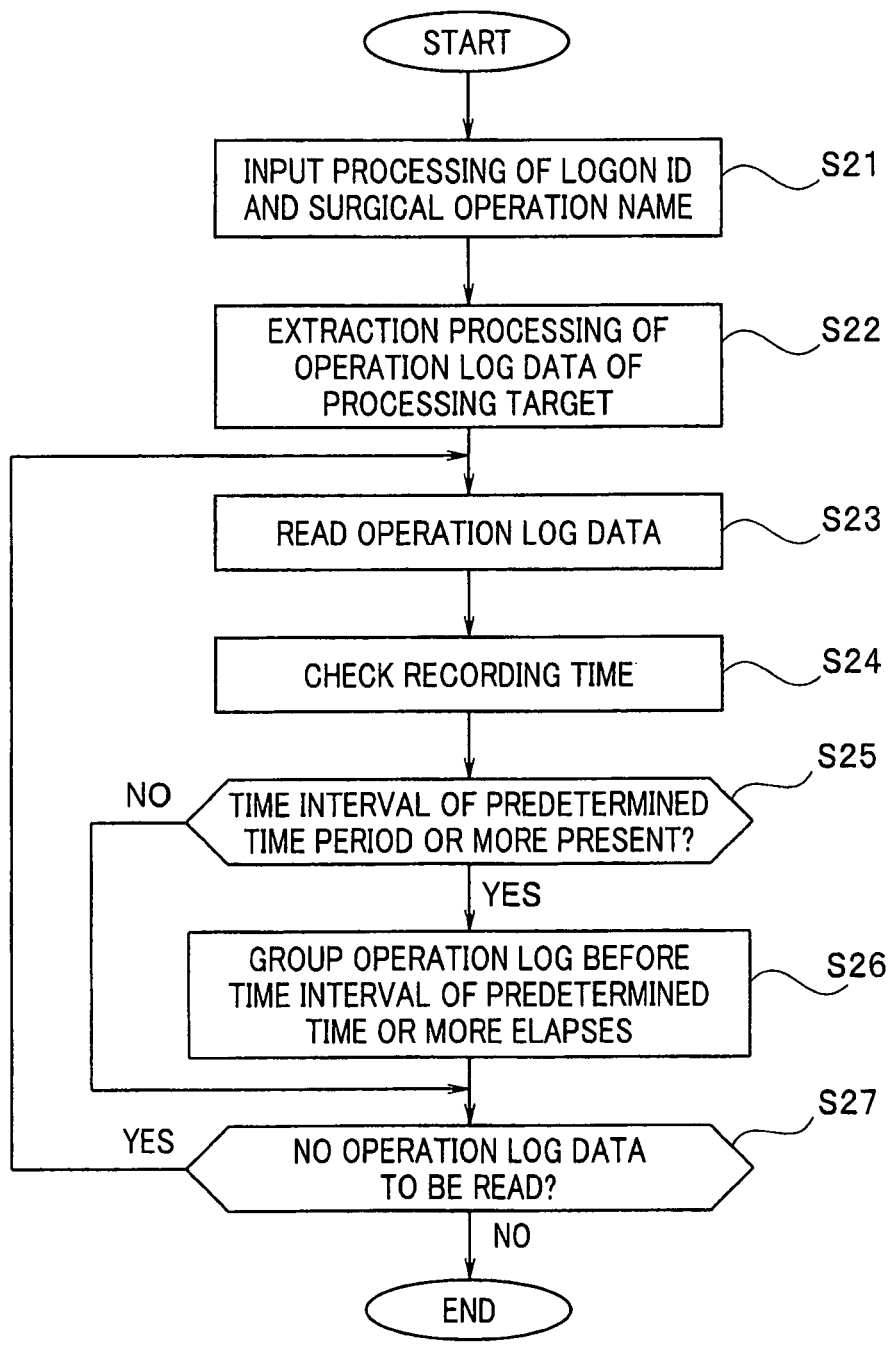

MEDICAL SUPPORT APPARATUS AND OPERATION METHOD OF MEDICAL SUPPORT APPARATUS

CROSS REFERENCE TO RELATED APPLICATION

This application is a continuation application of PCT/JP2014/062062 filed on May 1, 2014 and claims benefit of Japanese Application No. 2013-119151 filed in Japan on Jun. 5, 2013, the entire contents of which are incorporated herein by this reference.

BACKGROUND OF THE INVENTION

1. Field of the Invention

The present invention relates to a medical support apparatus that supports various settings according to scenes to various apparatuses for use in surgical operations, and an operation method of the medical support apparatus.

2. Description of the Related Art

Various medical apparatuses are installed in an operating room. The various medical apparatuses include various apparatuses such as a shadowless lamp, an endoscope apparatus, a pneumoperitoneum apparatus and an electric knife apparatus, and on/off settings, change of output set values and the like that are necessary for the respective apparatuses are performed in each scene during a surgical operation. Further, in the operating room, non-medical apparatuses such as an indoor light, a communication apparatus for communicating with an outside, a video apparatus for video recording and a teleconferencing system are also installed. For the non-medical apparatuses, on/off settings, change of output set values and the like that are necessary are performed in each scene during a surgical operation.

In general, the respective apparatuses in an operating room are intensively controlled by a system controller. A nurse in a sterilized zone in an operating room performs on/off, change of settings and the like of the respective apparatuses by operating an input apparatus such as an operation panel that is connected to the system controller, each time of scene change during a surgical operation. That is to say, a surgical operation is performed while on/off, change of set values and the like of the respective apparatuses are performed in response to scene change during the surgical operation.

Operation methods of the respective apparatuses differ from one another, and therefore when a nurse is not accustomed to the operations of the apparatuses, the nurse cannot perform the operations quickly. Therefore, there is proposed an endoscope surgery system that causes the operation screen of the medical apparatus in a surgical operation to be displayed on a display apparatus, and enables even a user who is not accustomed to an operation of the apparatus to use the apparatus efficiently, as disclosed in Japanese Patent Application Laid-Open Publication No. 2004-105533.

Further, a system is also put to practical use, which has a function of being capable of collectively changing settings and the like of the respective apparatuses which are set in advance for each scene with a one-touch operation to an input apparatus.

SUMMARY OF THE INVENTION

A medical support apparatus of one aspect of the present invention has a time interval determination section that determines whether or not a difference of recording times of two pieces of operation log data adjacent in time sequence has a time interval equal to or longer than a predetermined time period, with respect to the operation log data including identification information for identifying each of a surgical operator, a surgical operation and an apparatus to be controlled, operation contents for respective apparatuses to be controlled that are used at a time of the surgical operation, and a recording time, and a grouping section that groups a plurality of operation log data that continue in time sequence, with a difference of the recording times of the two pieces of operation log data adjacent in the time sequence being shorter than the predetermined time period, as one scene, when it is determined that the difference of the recording times of the two pieces of operation log data adjacent in time sequence has the time interval equal to or longer than the predetermined time period in the time interval determination section.

An operation method of a medical support apparatus of one aspect of the present invention is such that a time interval determination section of the medical support apparatus having operation log data including identification information for identifying each of a surgical operator, a surgical operation and an apparatus to be controlled, operation contents for respective apparatuses to be controlled that are used at a time of the surgical operation, and a recording time determines whether or not a difference of recording times of two pieces of operation log data adjacent in time sequence has a time interval equal to or longer than a predetermined time period, with respect to the operation log data, and a grouping section that groups the operation log data of the medical support apparatus groups a plurality of operation log data that continue in time sequence, with a difference of the recording times of the two pieces of operation log data adjacent in time sequence being shorter than the predetermined time period, as one scene, when it is determined that the difference of the recording times of the two pieces of operation log data adjacent in time sequence has the time interval equal to or longer than the predetermined time period by the time interval determination section.

BRIEF DESCRIPTION OF THE DRAWINGS

FIG. 6 is a diagram showing examples of set states and output states of respective apparatuses in respective stages in the surgical operation of FIG. 5;

FIG. 9 is a diagram showing a configuration example of a teleconference connection information table TBL1 that stores teleconference connection information, according to the first embodiment of the present invention;

FIG. 10 is a diagram showing an example of a correspondence table TBL2 of a scene and a checklist, according to the first embodiment of the present invention;

FIG. 11 is a diagram showing an example of the checklist according to the first embodiment of the present invention;

FIG. 12 is a diagram showing another example of the checklist according to the first embodiment of the present invention;

FIG. 13 is a diagram showing a configuration example of operation log data DDA that is already stored in a storage apparatus 42, according to a second embodiment of the present invention; and FIG. 14 is a flowchart showing an example of a flow of processing of a scene-number-added operation log data creation program P1A, according to the second embodiment of the present invention.

DETAILED DESCRIPTION OF THE PREFERRED EMBODIMENTS

Hereinafter, embodiments of the present invention will be described with reference to the drawings.

First Embodiment

Figure 1:
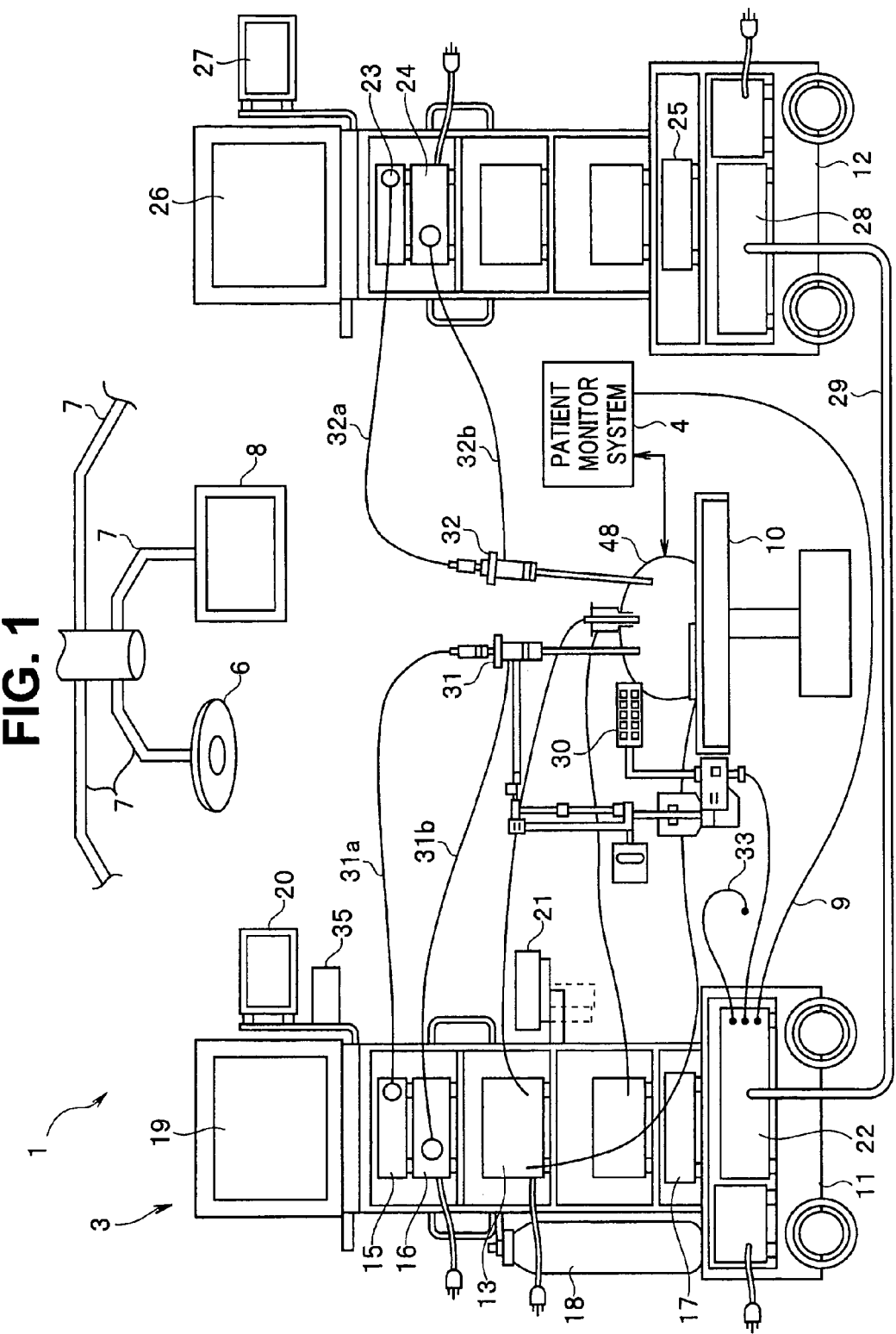
FIG. 1 is a configuration diagram of a surgical system 1 according to a first embodiment of the present invention.

First of all, an entire configuration of a surgical system 1 that is disposed in an operating room will be described with use of FIG. 1. FIG. 1 is a configuration diagram of the surgical system 1 according to the embodiment of the present invention. The surgical system 1 includes a plurality of medical apparatuses, and a plurality of non-medical apparatuses.

As shown in FIG. 1, in the operating room, a patient bed 10 on which a patient 48 lies down, a plurality of shadowless lamps 6, a display apparatus 8, and a medical system 3 are disposed. The medical system 3 has a first cart 11 and a second cart 12. The respective shadowless lamps 6 and the display apparatus 8 are fixed to a ceiling of the operating room by an arm 7.

On the first cart 11, apparatuses such as an electric knife apparatus 13, a pneumoperitoneum apparatus 14, an endoscope camera apparatus 15, a light source apparatus 16 and a video tape recorder (VTR) 17, and a gas cylinder 18 charged with carbon dioxide, for example, are mounted as medical apparatuses that are apparatuses to be controlled. The endoscope camera apparatus 15 is connected to a first endoscope 31 via a camera cable 31a.

The light source apparatus 16 is connected to the first endoscope 31 via a light guide cable 31b. Further, on the first cart 11, a display apparatus 19, a first intensive display panel 20, an operation panel 21 and the like are mounted. The display apparatus 19 is a TV monitor, for example, that displays endoscopic images and the like.

The intensive display panel 20 is display means capable of causing all data in a surgical operation to be selectively displayed. The operation panel 21 is configured by, for example, a display section such as a liquid crystal display, and, for example, a touch sensor that is integrally provided on the display section, and serves as an intensive operation apparatus that is operated by a nurse or the like who is in an unsterilized zone.

Furthermore, on the first cart 11, a system controller 22 that is an intensive control apparatus is mounted. To the system controller 22, the respective shadowless lamps 6, the electric knife apparatus 13, the pneumoperitoneum apparatus 14, the endoscope camera apparatus 15, the light source apparatus 16 and the VTR 17 which are described above are connected via a communication line not illustrated. A headset type microphone 33 can be connected to the system controller 22, and the system controller 22 recognizes voice that is inputted from the microphone 33, and can control the respective apparatuses according to a voice of a surgeon.

Further, the first cart 11 is provided with an RFID (radio frequency identification) terminal 35 capable of reading/writing individual ID information of articles by radio according to ID tags that are buried in the first endoscope 31, a treatment instrument of the electric knife apparatus 13 and the like.

Meanwhile, on the second cart 12, an endoscope camera apparatus 23, a light source apparatus 24, an image processing apparatus 25, a display apparatus 26 and a second intensive display panel 27 that are apparatuses to be controlled are mounted. The endoscope camera apparatus 23 is connected to a second endoscope 32 via a camera cable 32a. The light source apparatus 24 is connected to the second endoscope 32 via a light guide cable 32b.

The display apparatus 26 displays endoscopic images and the like that are captured by the endoscope camera apparatus 23. The second intensive display panel 27 enables all data in a surgical operation to be selectively displayed.

The endoscope camera apparatus 23, the light source apparatus 24 and the image processing apparatus 25 are connected to a junction unit 28 that is mounted on the second cart 12 via a communication line not illustrated. The junction unit 28 is connected to the system controller 22 which is mounted on the first cart 11 described above by a junction cable 29.

In this manner, the system controller 22 can intensively control the endoscope camera apparatus 23, the light source apparatus 24 and the image processing apparatus 25 which are mounted on the second cart 12, and the electric knife apparatus 13, the pneumoperitoneum apparatus 14, the endoscope camera apparatus 15, the light source apparatus 16 and the VTR 17 which are mounted on the first cart 11, the respective shadowless lamps 6, the respective display apparatuses 8 and indoor lights (not illustrated). Therefore, when communication is performed between the system controller 22 and the apparatuses, the system controller 22 can display a setting screen of set states, operation switches and the like of the connected apparatuses, on the liquid crystal display of the aforementioned operation panel 21. Further, in the system controller 22, a desired operation switch is touched, and a touch sensor in a predetermined region is operated, whereby an operation input of change of a set value or the like can be performed.

A remote controller 30 is a second intensive operation apparatus that is operated by a surgical operator and the like who are in a sterilized zone, and operation of other apparatuses with which communication is established is enabled via the system controller 22.

The system controller 22 is connected to a patient monitor system 4 by a cable 9, and the patient monitor system 4 analyzes living body information, and can cause the analysis result to be displayed on a necessary display apparatus.

Further, to the system controller 22, an infrared communication port (not illustrated) that is communication means is attached. The infrared communication port is provided at a position which is easily irradiated with infrared rays, in a vicinity of the display apparatus 19 or the like, and is connected with the system controller 22 via a cable.

Figure 2:
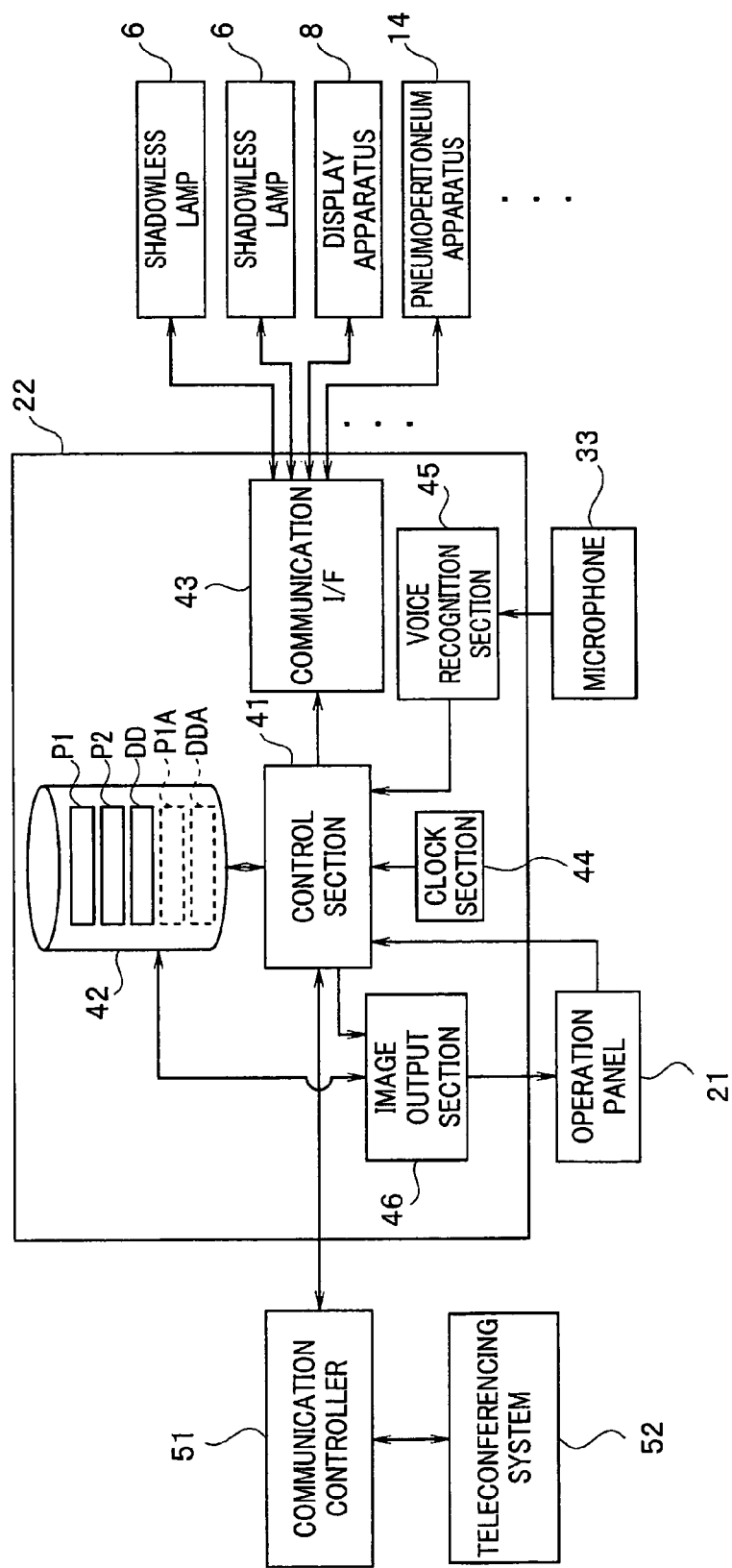
FIG. 2 is a block diagram for explaining a configuration of a system controller 22 according to the first embodiment of the present invention.

FIG. 2 is a block diagram for explaining a configuration of the system controller 22.

The system controller 22 is configured by including a control section 41, a storage apparatus 42, a communication interface section (hereinafter, called a communication I/F) 43, a clock section 44, a voice recognition section 45, and an image output section 46.

The control section 41 includes a central processing unit (hereinafter, called a CPU), a ROM and a RAM, and controls actions of the respective sections in the control section 41, and the respective medical apparatuses and the respective non-medical apparatuses of the surgical system 1 by the CPU reading and executing various programs that are stored in the ROM or the storage apparatus 42 which will be described later.

The storage apparatus 42 is a storage section such as a hard disk device, and stores various programs and various data. The storage apparatus 42 is connected to the control section 41, and read and write of various programs and various data with respect to the storage apparatus 42 are performed under control of the control section 41. In the storage apparatus 42, an operation log collection program P1, an apparatus setting reproduction program P2 and operation log data DD, which will be described later, are stored.

The communication I/F 43 is an interface circuit section between the various medical apparatuses such as the pneumoperitoneum apparatus 14 and the various non-medical apparatuses such as the display apparatus 8, and the control section 41. Control signals from the control section 41 are outputted to the respective apparatuses via the communication I/F 43, and various signals from the respective apparatuses are inputted to the control section 41 via the communication I/F 43.

The clock section 44 is a circuit that generates time data to output the time data. The clock section 44 outputs the time data to the control section 41.

The voice recognition section 45 receives a voice signal from the microphone 33, recognizes a voice which is given by a surgical operator or a nurse, and outputs the recognized voice data to the control section 41. For example, a surgical operator can input a desired command by voice to a desired apparatus by voice.

The image output section 46 is a processing section that reads various data from the storage apparatus 42 under control of the control section 41, generates image data of various screens and the like such as a scene selection screen which will be described later, and outputs the image data to the operation panel 21.

The control section 41 is also connected to the operation panel 21, receives an input signal to a touch sensor from the operation panel 21, and outputs a control signal and a data signal for causing the display section of the operation panel 21 to display various screens and various data to the image output section 46.

Furthermore, a communication controller 51 is connected to the system controller 22. The communication controller 51 is connected to a teleconferencing system 52. More specifically, the communication controller 51 is connected to the control section 41, and performs actuation, control and the like of the teleconferencing system 52 based on a control signal from the control section 41.

The teleconferencing system 52 is a system for the surgical operator in the operating room and a remote person (for example, a doctor) to perform a so-called teleconference, and is used to transmit a situation in a surgical operation to the remote person.

(Operation Log Data)

Next, a configuration of operation log data that is collected during a surgical operation, and is grouped according to scenes as will be described later, will be described.

Figure 3:
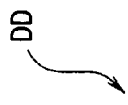
FIG. 3 is a diagram showing a configuration of operation log date according to the first embodiment of the present invention.

The control section 41 records data of operations of the operation panel 21 which are performed during a surgical operation as the operation log data. FIG. 3 is a diagram showing a configuration of the operation log data.

As shown in FIG. 3, the operation log data DD that is stored in the storage apparatus 42 includes data of a plurality of items that are a scene number (scene #), a time, a logon identifier (hereinafter, called a logon ID), a surgical operation name, an apparatus name, a function name and a changed value.

The scene number is an identifier of a scene that changes with a lapse of time in one surgical operation. In this case, the identifier is a scene number, but does not have to be a number. In one scene in a surgical operation, processing or treatment is performed by the surgical operator in a state in which set states and output states of the respective apparatuses in the surgical system 1 do not change. When the set state or the output state of at least one of the apparatuses is changed so as to differ from the set states and the output states of the respective apparatuses in the surgical system 1 in a certain one scene, it is determined that change of the scene is made, and the one scene and a following scene after the set state or the like is changed are not the same one scene.

For example, a scene of a preparation stage immediately before a surgical operation is started is a scene in which the indoor lamp in the operating room is in an on state, the shadowless lamp 6 is in an off state, and power supply of the other apparatuses is in an on state. When the scene shifts from the scene to a scene of a stage of inserting a trocar, various operations such as turning off the indoor light, changing an output pressure of the pneumoperitoneum apparatus 14 to a predetermined pressure, and turning on the light source apparatus 16 are performed. Furthermore, when the scene shifts to a scene of a stage of resection extent identification, after trocar insertion, output of the pneumoperitoneum apparatus 14 is changed, and feeding of $CO_2$ is performed.

As above, while certain processing or treatment is performed, the set states and the output states of the respective medical apparatuses and the respective non-medical apparatuses in the surgical system 1 are not changed, but when other processing or treatment is performed, the set states and the output states of the respective medical apparatuses and the respective non-medical apparatuses in the surgical system 1 are changed.

Therefore, the scene refers to a situation in which processing or treatment is performed in a state in which the set states and the output states of the respective medical apparatuses and the respective non-medical apparatuses in the surgical system 1 are not changed.

In FIG. 3, a time refers to a time when an operation takes place, in other words, a time when the operation log data is recorded in the storage apparatus 42. Here, a recording time is constituted of a year, a month, a day, an hour, a minute and a second.

The logon ID refers to information for identifying a surgical operator who performs a surgical operation.

A surgical operation name refers to a title of a surgical operation to be performed.

An apparatus name refers to a name of a medical apparatus or a non-medical apparatus that is an operation target in the surgical system 1.

The function name refers to a name of a function of an operation. For example, the function name includes switch of on/off, change of a set value, switch of an input channel and the like.

The changed value refers to information showing a content of an operation, and is information such as on, off, a changed set value, and a changed output level.

The operation log data shown in FIG. 3 is created by processing that will be described later being performed.

As shown in FIG. 3, one operation log data in which the scene number is "1", the time is "2013/2/1 10:00:15", the logon ID is "1", the surgical operation name is "ABC", the apparatus name is "Light1", the function name is "ON/OFF" and the changed value is "ON" is stored as first operation log data of the scene number "1", after the scene number of "10". After the first operation log data of the scene number "1", seven pieces of operation log data are recorded. That is to say, FIG. 3 shows that the operation log data from the first operation log data through one operation log data in which the scene number is "1", the time is "2013/2/1 10:00:45", the logon ID is "1", the surgical operation name is "ABC", the apparatus name is "Light2", the function name is "Intensity" and the changed value is "1" is recorded as the operation log data of the scene number "1".

FIG. 3 further shows that operation log data in which the scene number is "2", the time is "2013/2/1 10:12:00", the logon ID is "1", the surgical name is "ABC", the apparatus name is "Insuflator", the function name is "Start/Stop", and the changed value is "Start", and following operation log data are recorded as the operation log data of the scene number "2".

A time interval between the operation log data of the scene 1 and the scene 2 is a time period equal to or longer than ten minutes.

The system controller 22 groups the operation log data according to scenes by monitoring operations that are inputted to the operation panel 21, collecting the operation log data, automatically determining a pause of the scene, and adding the scene numbers, creates the operation log data DD having the scene numbers as shown in FIG. 3 and stores the operation log data DD in the storage apparatus 42, by executing the operation log correction program P1.

(Operation)

Next, grouping processing of the operation log data by the operation log collection program P1 will be described. The operation log collection program P1 groups the operation log data while collecting the operation log data during a surgical operation, and generates scene-number-added operation log data. Therefore, the system controller 22 which executes the operation log collection program P1 configures a medical support apparatus that groups the operation log data.

Figure 4:
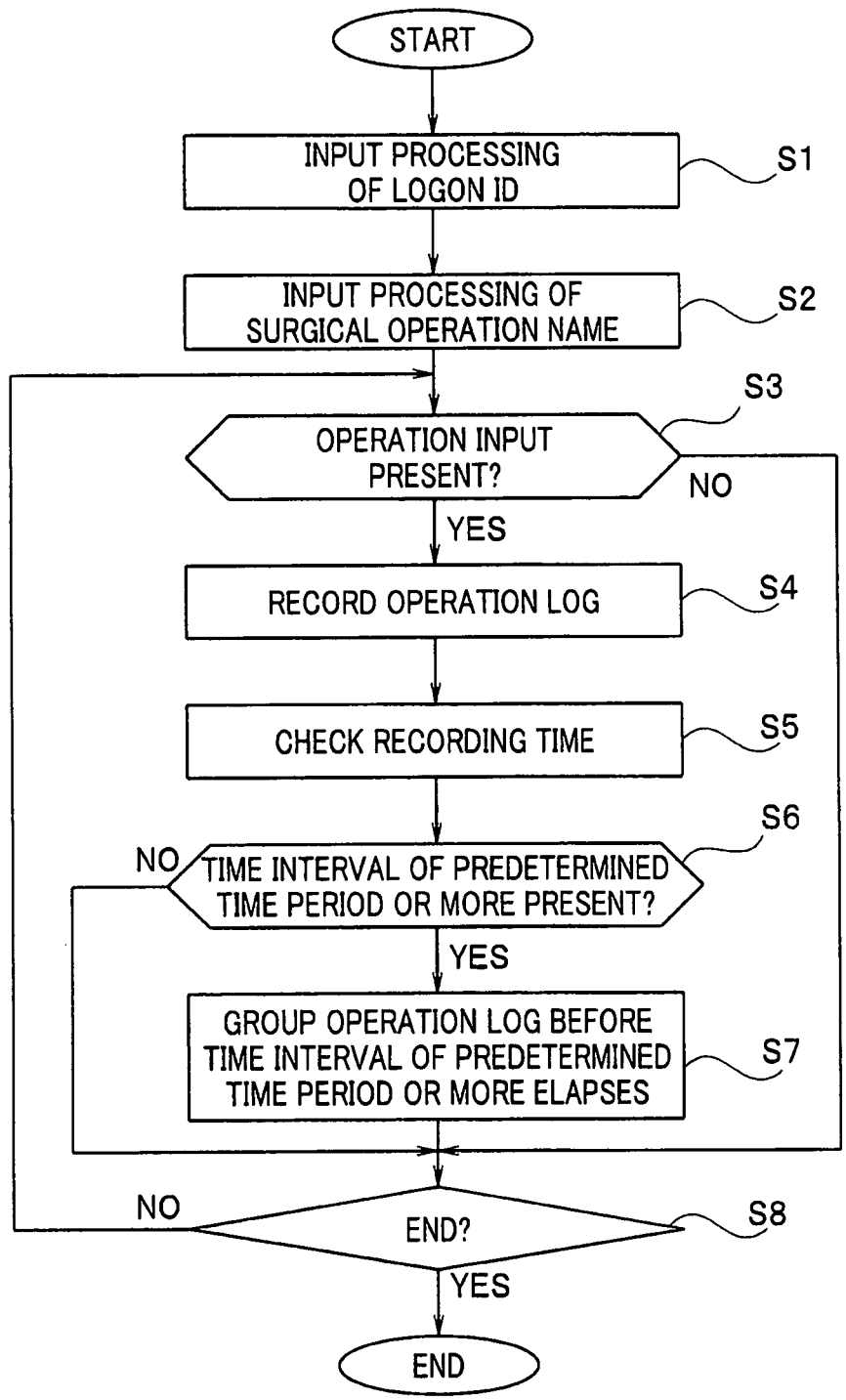
FIG. 4 is a flowchart showing a flow of processing of an operation log collection program P1 according to the first embodiment of the present invention.

The CPU of the control section 41 reads the operation log collection program P1 which is stored in the storage apparatus 42 and executes the operation log collection program P1, whereby processing in FIG. 4 is executed.

FIG. 4 is a flowchart showing a flow of the processing of the operation log collection program P1.

For example, when a nurse inputs an instruction of creation of the operation log data according to scenes in the operation panel 21 of the system controller 22, the control section 41 reads and executes the operation log collection program P1 from the storage apparatus 42.

The control section 41 firstly displays the input field for causing the logon ID of the surgical operator to be inputted as well as a predetermined message, on the screen of the display section of the operation panel 21, and executes input processing of the logon ID that causes a surgical operator or a nurse to input the logon ID of the surgical operator to the input field (S1).

When the control section 41 ends input processing of the logon ID, the control section 41 displays an input field to which a surgical operation name to be performed is inputted as well as a predetermined message, on a screen of the display section of the operation panel 21, and executes input processing of the surgical operation name which causes the surgical operator or the nurse to input the surgical operation name to the input field (S2).

After the processing of S2, the control section 41 determines whether or not an operation input to the operation panel 21 is present (S3). That is to say, presence or absence of an operation to the operation panel 21 is determined.

When the operation input is present (S3: YES), the control section 41 performs record of operation log (S4). In S4, the data of the items of the time, the logon ID, the surgical operation name, the apparatus name, the function name and the changed value in the operation log data in FIG. 3 are recorded. That is to say, the operation log data other than the scene number are added to the operation log data DD.

Next, the control section 41 calculates a difference between a recording time tp of the operation log data which is recorded this time, and a recording time tf of the operation log data which is recorded at a previous time, and performs check of the recording time for comparing an interval of the recording time and a predetermined time period TH (S5).

The control section 41 determines whether or not a time interval equal to or longer than the predetermined time period TH is present between the recording time tp of the operation log data recorded this time and the recording time tf of the operation log data recorded at the previous time (S6). That is to say, the processing in S6 configures a time interval determination section that determines whether or not the difference of the recording times of two pieces of operation log data adjacent in time sequence has the time interval equal to or longer than the predetermined time period TH, with respect to the operation log data including identification information for identifying each of a surgical operator, a surgical operation and apparatuses to be controlled, and operation contents for the respective apparatuses to be controlled that is used at the time of the surgical operation. In particular, in S6 that is the time interval determination section, when the operation log data of the operations for the respective apparatuses to be controlled which are performed during the surgical operation is stored in the storage apparatus 42, it is determined whether or not the difference of the recording times of the two pieces of operation log data which are adjacent in time sequence has the time interval equal to or longer than the predetermined time interval TH.

If there is the time interval equal to or longer than the predetermined time period TH (S6: YES), the control section 41 groups the operation log data before the time interval equal to or longer than the predetermined time period TH elapses (S7). That is to say, the control section 41 groups the operation log data which is the operation log data up to the recording time tf when recording is performed at the previous time, and is not assigned with the scene number, as one group.

For example, in the case of FIG. 3, when the predetermined time period TH is assumed to be ten minutes, the time intervals between the two pieces of adjacent operation log data are shorter than the predetermined time period TH from the first operation log data at the time "2013/2/1 10:00:15" through the following seven pieces of operation log data. However, a time difference between a time "2013/2/1 10:01:45" and a time "2013/2/1 10:12:00" is equal to or longer than ten minutes, and therefore, the control section 41 groups the operation log data from the time "2013/2/1 10:00:15" through the time "2013/2/1 10:01:45" and assigns the operation log data with the scene number, when the operation log data at the time "2013/2/1 10:12:00" is recorded. Here, the scene number is determined in such a manner that "1" is incremented by one, and the operation log data is grouped by being assigned with the scene number "1" here.

That is to say, the processing in S7 configures a grouping section that groups a plurality of operation log data which continue in time sequence, with the difference of the recording times of the two pieces of operation log data adjacent in time sequence is shorter than the predetermined time period TH, as one scene, when it is determined that the difference of the recording times of the two pieces of operation log data which are adjacent in time sequence has the time interval equal to or longer than the predetermined time period TH in the processing in S6. In particular, in S7, the scene number as the same scene identification information is assigned to the plurality of operation log data which are grouped as one scene.

Next, the control section 41 determines whether or not an end instruction is made (S8). When an end command of an end of the surgical operation or an end of the record is inputted to the operation panel 21 (S8: YES), the processing ends. When the end command of the surgical operation is not inputted to the operation panel 21, the processing returns to S3.

Further, when an operation input is absent (S3: NO), the processing shifts to S8. Furthermore, when the time interval equal to or longer than the predetermined time period TH does not exist between the recording time tp of the operation log data which is recorded this time, and the recording time tf of the operation log data which is recorded at the previous time (S6: NO), the processing also shifts to S8.

By the above processing being executed, the operation log data DD shown in FIG. 3 is stored in the storage apparatus 42.

Figure 5:
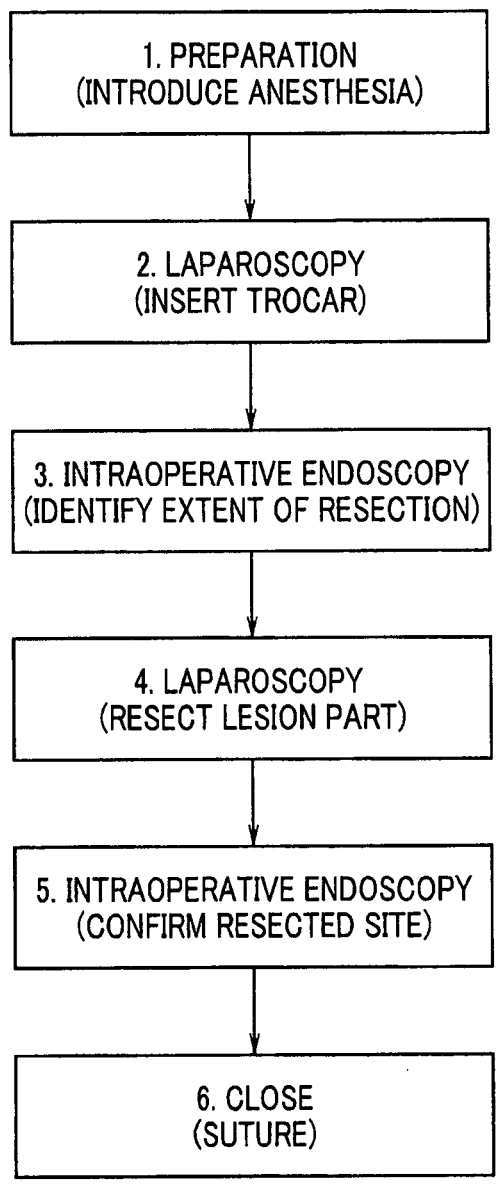
FIG. 5 is a diagram for explaining a flow of scenes of a certain surgical operation performed by a certain surgical operator.

Here, explanation will be made by a specific example of the surgical operation being cited. FIG. 5 is a view for describing a flow of a scene of a certain surgical operation that is performed by a certain surgical operator.

As shown in FIG. 5, the certain surgical operation is assumed to have a plurality of stages including a stage of "1. PREPARATION" for introduction of anesthesia firstly, a stage of "2. LAPAROSCOPY" for trocar insertion after "1. PREPARATION", a stage of "3. INTRAOPERATIVE ENDOSCOPY" for resection extent identification after "2. LAPAROSCOPY", a stage of "4. LAPAROSCOPY" for lesion part resection after "3. INTRAOPERATIVE ENDOSCOPY", a stage of "5. INTRAOPERATIVE ENDOSCOPY" for resected site confirmation after "4. LAPAROSCOPY", and a stage of "6. CLOSE" for suture after "5. INTRAOPERATIVE ENDOSCOPY".

The surgical operation in FIG. 5 includes a series of six stages as above. When in the six stages, a certain stage shifts to a next stage, change of processing that is performed in the next stage or the set states or output states of the respective apparatuses in the operating room which are necessary for the processing is performed.

FIG. 6 is a diagram showing examples of the set states and the output states of the respective apparatuses in the respective stages in the surgical operation. FIG. 6 is an example in which a surgical system has shadowless lamps 1 and 2, an indoor light, a light source apparatus 1 for a laparoscope, a light source apparatus 2 for an endoscope, and monitors 1 and 2 as display apparatuses. In the surgical operation shown in FIG. 6, processing or treatment from the stage "1. PREPARATION" to the stage "6. CLOSE" is performed with a lapse of a time t. As shown in FIG. 6, when the stage "1. PREPARATION" is started, the respective apparatuses are changed from set states and output states of initial states before the surgical operation is started to set states and output states shown in the stage "1. PREPARATION" in FIG. 6.

That is to say, before the processing or the treatment in the stage "1. PREPARATION", operations of turning "on" the shadowless lamp 1 and the shadowless lamp 2, turning "on" the indoor lights, setting the output set value of the pneumoperitoneum apparatus at "12 mmHg" and the like are performed in the operation panel 21 by a nurse. Since operations are performed continuously, differences among the recording times of the plurality of operation log data in a range of the scene number of "1" in FIG. 3 is within the predetermined time period (ten minutes).

After the setting operations for the stage "1. PREPARATION" as above are performed, processing or treatment of introduction of anesthesia of the stage "1. PREPARATION" is executed. Processing or treatment of introduction of anesthesia takes a time period equal to or longer than the predetermined time period (ten minutes).

When the processing or treatment of the stage "1. PREPARATION" is ended, and the stage "2. LAPAROSCOPY" is started, the respective apparatuses are changed from the set states and the output states for the stage "1. PREPARATION" to set states and output states shown in the stage "2. LAPAROSCOPY" in FIG. 6.

That is to say, before the processing or treatment in the stage "2. LAPAROSCOPY", operations of turning "off" the shadowless lamp 1, "dimming" the shadowless lamp 2, turning "off" the indoor lights, setting the output set value of the pneumoperitoneum apparatus at "15 mmHg", and turning on the light source apparatus 1 are performed in the operation panel 21 by the nurse. Since the operations are continuously performed, the differences among the recording times of the plurality of operation log data in a range of the scene number of "2" in FIG. 3 are within the predetermined time period (ten minutes), but processing or treatment of trocar insertion takes a time period equal to or longer than the predetermined time period (ten minutes).

After the setting operation for the stage "2. Laparoscopy" as above is performed, and extinction of the shadowless lamps and the indoor lights, lighting of the lamp of the laparoscope, and start of pneumoperitoneum are executed, processing or treatment of trocar insertion of the stage "2. Laparoscopy" is executed.

At the stage of "3. INTRAOPERATIVE ENDOSCOPY" for identifying the extent of resection which is performed after the stage "2. Laparoscopy", the light source apparatus 1 is dimmed, the light source apparatus 2 is turned on, and output images on the monitors 1 and 2 are set so that both of an endoscopic image and a laparoscopic image are outputted.

After the setting operation for the stage "3. INTRAOPERATIVE ENDOSCOPY" like this is performed, and lighting of the lamp of the endoscope, and switch of the monitor output image are executed, the treatment of the stage "3. INTRAOPERATIVE ENDOSCOPY" is executed.

Thereafter, the setting operations for the respective stages of "4. LAPAROSCOPY" and "5. INTRAOPERATIVE ENDOSCOPE" are similarly performed, after which, processing or treatment in each of the stages is executed.

Subsequently, after resection of the lesion part is completed, and confirmation of the sutured region is performed with an endoscope, the shadowless lamps 1 and 2 and the indoor lights are lit, the lamps of the light source apparatuses for the laparoscope and the endoscope are turned off, the processing of the last stage "6. CLOSE" which stops the pneumoperitoneum apparatus is performed, and the surgical operation is ended. When end of the surgical operation is instructed, the operation log data DD as in FIG. 3 is stored in the storage apparatus 42.

As above, the predetermined time period TH is determined based on the time taken for each processing or treatment in the surgical operation, and based on the predetermined time period TH which is determined, the operation log data can be grouped and classified according to the scenes at the time of collection of the operation logs.

The operation log data DD shown in FIG. 3 includes data of all logon IDs of all surgical operations. However, since the operation log data DD includes the information of the surgical operation names and the logon IDs, a nurse specifies the surgical operation name and the logon ID, and can search for and extract the operation log data to be used in the surgical operation from the operation log data DD, when the surgical operation is performed.

Figure 7:
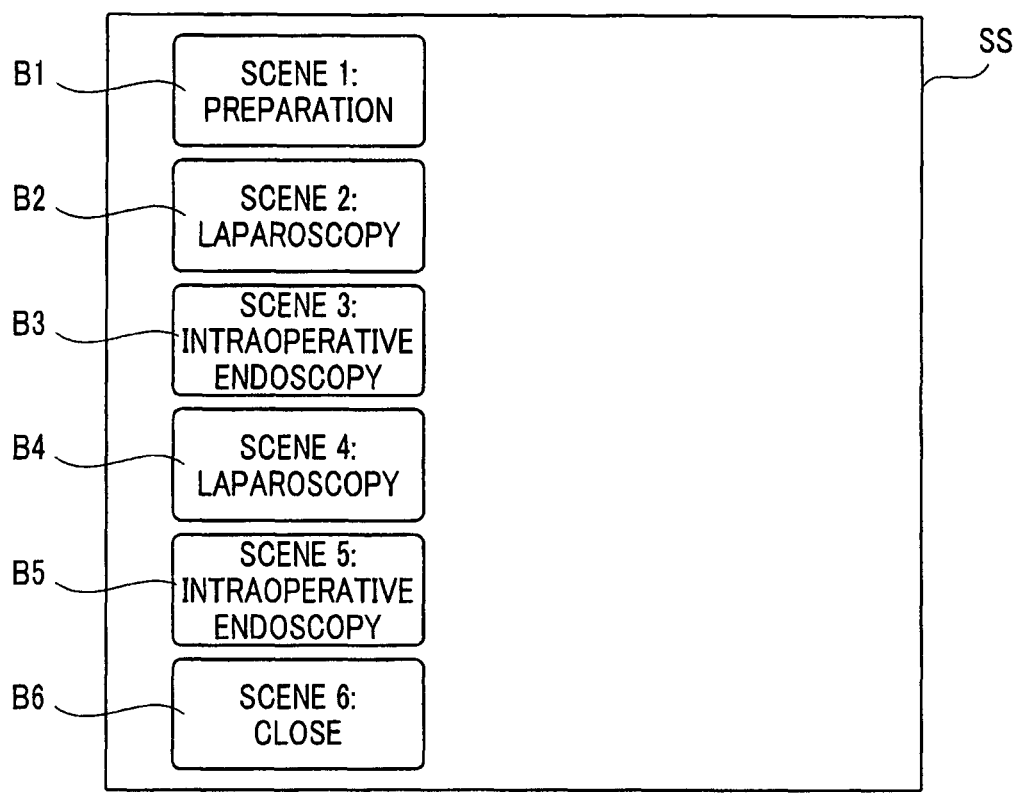
FIG. 7 is a diagram showing an example of a scene selection screen SS which is displayed on a screen of a display device of an operation panel 21 when set states and output states of respective apparatuses in an operating room are changed, according to the first embodiment of the present invention.

With respect to the extracted operation log data DD1, a name for each of the scenes is assigned, and a scene selection screen as in FIG. 7 can be created.

FIG. 7 is a diagram showing an example of a scene selection screen SS that is displayed on the screen of the display device of the operation panel 21, when the set states and the output states of the respective apparatuses in the operating room are changed.

The scene selection screen SS includes a plurality of selection buttons B1 to B6 for selecting the respective scenes corresponding to the respective stages included in the surgical operation. The names of the scenes are set to display sections of the respective buttons.

The screen as in FIG. 7 is created by a nurse in such a manner as to assign the names of the scenes to the screen of a template that is prepared in advance, for example.

By touching a desired button on the screen in FIG. 7 which is displayed on the screen of the operation panel 21, the nurse who is a user can select a desired scene.

Next, a case in which a surgical operation is performed with use of the operation log data DD which is collected as above, and the scene selection screen SS in FIG. 7 will be described.

Figure 8:
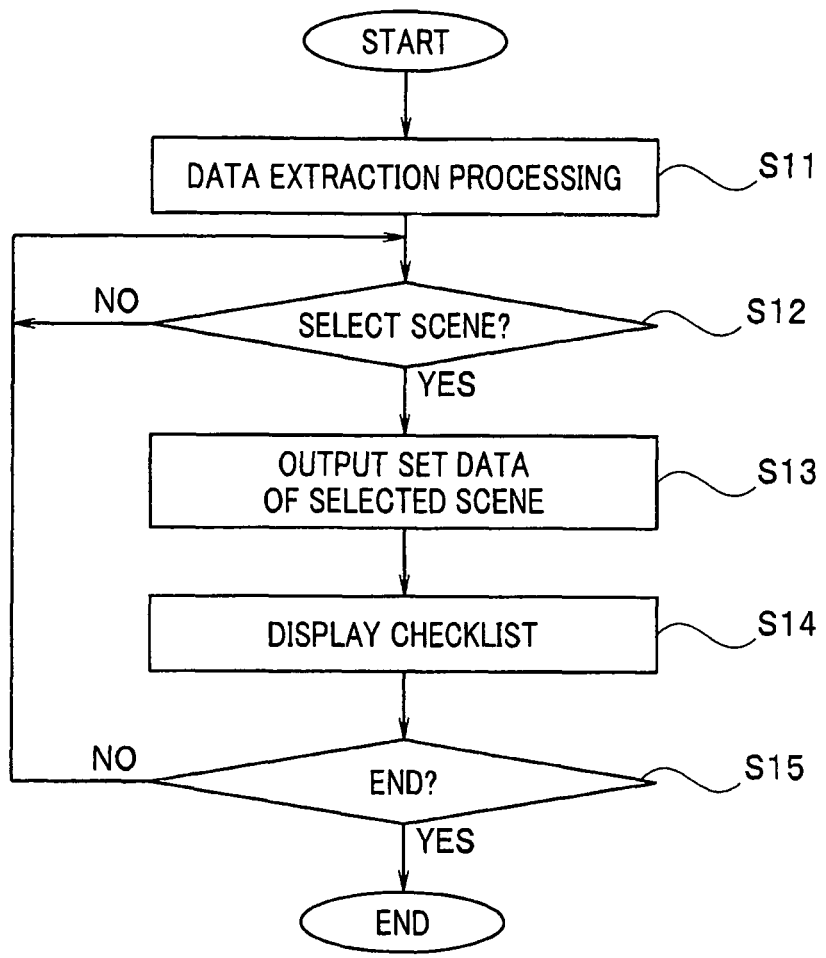
FIG. 8 is a flowchart showing a flow of processing of an apparatus setting reproduction program P2, according to the first embodiment of the present invention.

FIG. 8 is a flowchart showing a flow of processing of an apparatus setting reproduction program P2.

The processing in FIG. 8 is executed by a nurse inputting a predetermined instruction command to the operation panel 21. Therefore, when the control section 41 senses input of the instruction command, the control section 41 reads the apparatus setting reproduction program P2 from the storage apparatus 42 and executes the apparatus setting reproduction program P2.

First, the control section 41 executes data extraction processing (S11). In the data extraction processing, the control section 41 displays the input field for causing the surgical operator and the surgical operation name to be inputted together with a predetermined message, on the screen of the display section of the operation panel 21, and causes the surgical operator or the nurse to input the surgical operator and the surgical operation name to the input field, and the operation log data corresponding to the surgical operator and the surgical operation name which are inputted is extracted.

That is to say, from the tremendous operation log data DD, only operation log data DD1 to which the surgical operator and the surgical operation name of the surgical operation to be performed thereafter correspond is extracted, and with use of the extracted operation log data DD1, reproduction processing of the apparatus settings which will be described next is performed. Therefore, the processing in S11 configures an operation log data extraction section that extracts the operation log data corresponding to identification information of the surgical operator and the surgical operation.

Subsequently, the control section 41 determines presence or absence of scene selection (S12). Presence or absence of the scene selection is determined based on whether or not any one of the selection buttons B1 to B6 in FIG. 7 is selected by being touched by the finger of a nurse.

When scene selection is absent (S12: NO), no processing is performed.

When scene selection is present (S12: YES), the control section 41 outputs the setting data of the selected scene to the respective apparatuses via the communication I/F 43 (S13). For example, when the scene 1 is selected, the operation log data with the scene number of "1" are extracted, settings of changed values with respect to the specified functions are outputted via the communication I/F 43 to the respective apparatuses specified in the respective log data. As a result, the set states or the output states of the respective apparatuses corresponding to the stage "1. PREPARATION" in FIG. 6 are collectively changed by the control section 41, and therefore, the surgical operation time period is also reduced.

Therefore, the processing in S12 configures a scene selection section that selects one scene from the plurality of scenes which are grouped by S7 which is the grouping section, and the processing in S13 configures a scene operation signal output section that outputs operation signals to the respective apparatuses to be controlled based on information and operation contents of the apparatuses to be controlled that are included in each of a plurality of operation log data with respect to the one scene selected in S12.

Note that when a setting of using the teleconferencing system 52 is included in the settings outputted in S13, the control section 41 controls the communication controller 51, and actuates the teleconferencing system 52.

For this purpose, teleconference connection information for telephone connection with an outside for teleconference is stored in the storage apparatus 42 in advance.

FIG. 9 is a diagram showing a configuration example of a teleconference connection information table TBL1 that stores the teleconference connection information.

The teleconferencing system 52 is a system that performs communication by voice and images with a remote person by using a telephone line, and can establish communication with a teleconferencing system of a counterpart by calling a designated telephone number.

Note that here, the teleconferencing system 52 is a system using a telephone line, but may be a system using a communication line of the Internet or the like.

Therefore, in the teleconference connection information table TBL1, the telephone number of the counterpart is registered in advance for each scene. When the scene selection is performed, the control section 41 checks registered information in the teleconference connection information table TBL1, and when the telephone number is registered, with respect to the selected scene, the control section 41 controls the communication controller 51, calls the registered telephone number and actuates the teleconferencing system 52, in S12.

Further, the control section 41 displays a checklist (S14). As for the checklist displayed in S14, confirmation matters necessary in the respective scenes are displayed on the screen of the display device of the operation panel 21, in a checklist format.

FIG. 10 is a diagram showing an example of a correspondence table TBL2 of the scene and the checklist. The correspondence table TBL2 in FIG. 10 is created in advance for each surgical name, for example, and is stored in the storage apparatus 42.

The correspondence table TBL2 is a table storing information of the checklist to be displayed for each scene. For example, the scene number "1" indicates displaying a checklist "ABC01".

FIG. 11 and FIG. 12 are diagrams showing examples of the checklist. As shown in FIG. 11 and FIG. 12, the checklist displays the items to be confirmed in the scene which is selected by a surgical operator and a nurse. Therefore, when the scene is selected and changed, a nurse or the like can perform necessary confirmation by looking at the items to be confirmed. That is to say, when the scene is selected, if a checklist that is set in advance with respect to the selected scene is present in the correspondence table TBL2, the checklists as shown in FIG. 11 and FIG. 12 are displayed on the screen of the display device of the operation panel 21.

Note that not only the checklist, but also a moving image necessary in the scene may be reproduced and displayed. The moving image is a moving image showing a state of treatment by a treatment instrument that is used in the selected scene, or the like.

Returning to FIG. 8, it is determined whether or not an instruction of end of execution of the apparatus setting reproduction program P2 is made in the operation panel 21 (S15). When the instruction of end of execution of the apparatus setting reproduction program P2 is made (S15: YES), the processing ends, and when the instruction is not made (S15: NO), the processing returns to S12.

Note that scene selection, and the instruction of end during execution of the apparatus setting reproduction program P2 may be enabled to be performed by voice using the microphone 33.

As above, according to the surgical system 1 of the present embodiment, the medical support apparatus which can automatically perform on/off setting and setting of the information such as change of the output set values of the respective apparatuses of each of the scenes of the surgical operation can be provided.

In particular, according to the surgical system 1 of the present embodiment, a job of performing on/off setting, change of the output set values and the like of the respective apparatuses for each scene becomes unnecessary.

Second Embodiment

In the first embodiment, grouping of the operation log data is performed by the operation log data being assigned with the scene number when the operation log data is collected, whereas in a second embodiment, grouping of the operation log data is performed by the operation log data which is already collected and recorded being assigned with the scene number.

A surgical system of the second embodiment has a configuration similar to the surgical system 1 of the first embodiment, and is similar to the configuration shown in FIG. 1 and FIG. 2. Therefore, in the present embodiment, the same components as in the first embodiment will be described with use of the same reference signs, explanation of the components already described will be omitted, and different components will be described.

As shown by the dotted line in FIG. 2, operation log data DDA is already stored in the storage apparatus 42. FIG. 13 is a diagram showing a configuration example of the operation log data DDA which is already stored in the storage apparatus 42. The operation log data DDA has the same configuration as the operation log data DD in FIG. 3 except for a point that the information of the scene numbers in the operation log data DD in FIG. 3 is not included.

Further, in the storage apparatus 42, a scene-number-added operation log data creation program P1A (shown by the dotted line in FIG. 2) for performing scene number assignment to the operation log data DDA is stored, and the control section 41 can assign scene numbers to the operation log data DDA and create the scene-number-added operation log data, by reading the scene-number-added operation log data creation program P1A from the storage apparatus 42 and executing the scene-number-added operation log data creation program P1A. Therefore, the system controller 22 which executes the scene-number-added operation log data creation program P1A configures a medical support apparatus that groups the operation log data.

FIG. 14 is a flowchart showing an example of a flow of processing of the scene-number-added operation log data creation program P1A.

For example, when a nurse inputs a creation instruction of the operation log data according to scenes in the operation panel 21 of the system controller 22, the control section 41 reads the scene-number-added operation log data creation program P1A from the storage apparatus 42 and executes the scene-number-added operation log data creation program P1A.

The control section 41 displays the input field for causing the logon ID of a surgical operator and a surgical operation name to be inputted as well as a predetermined message, on the screen of the display section of the operation panel 21, and executes input processing of the logon ID and the surgical operation name which causes the surgical operator or a nurse to input the logon ID of the surgical operator and the surgical operation name to the input field (S21).

When the input processing of the logon ID and the surgical operation name is ended, the control section 41 executes the extraction processing of the operation log data of a processing target corresponding to the logon ID and the surgical operation name which are inputted in S21 (S22). That is to say, only the operation log data which corresponds to the logon ID and the surgical operation name which are inputted in S21 are extracted from the operation log data DDA shown in FIG. 13.

For example, when the logon ID is "1", and the surgical operation name is "ABC", the operation log data of a time "2013/2/1 10:00:15" and the following times, which corresponds to the conditions are extracted in a case of FIG. 13.

Note that the extracted operation log data is in order of time.

Next, the control section 41 reads the operation log data extracted in S22 (S23). In the case of FIG. 13, the data at the time "2013/2/1 10:00:15" is read first.

The control section 41 checks the recording times of the read operation log data (S24). In S24, a difference between a recording time tp1 of the operation log data read in S23 and a recording time tf1 of the operation log data read at the previous time is calculated, and check of the recording times for comparing an interval of the recording times is performed (S24).

In the case of the first operation log data, the operation log data which is read at the previous time is absent, but in the case of the operation log data which is read at the second time and the following times, the difference between the recording time tp1 of the operation log data which is read this time and the recording time to of the operation log data which is read at the previous time is calculated.

The control section 41 determines whether or not a time interval equal to or longer than the predetermined time period TH is present between the recording time tp of the operation log data which is read this time and the recording time tf of the operation log data which is read at the previous time, as the result of the check in S24 (S25).

Therefore, the processing of S25 configures the time interval determination section which determines whether or not the difference of the recording times of the two pieces of operation log data adjacent in time sequence has the time interval equal to or longer than the predetermined time period, with respect to the operation log data including identification information for identifying each of a surgical operator, a surgical operations and apparatuses to be controlled, operation contents for the respective apparatuses to be controlled which are used at the time of the surgical operation, and the recording times. In particular, in the time interval determination section of S25, it is determined whether or not the difference of the recording times of the two pieces of operation log data which are adjacent in time sequence has the time interval equal to or longer than the predetermined time period TH, with respect to the operation log data of the operations for the respective apparatuses to be controlled which are stored in the storage apparatus 42.

If the time interval equal to or longer than the predetermined time period TH is present (S25: YES), the control section 41 groups the operation log data before the time interval equal to or longer than the predetermined time period TH elapses (S26). That is to say, the control section 41 groups the operation log data which is the operation log data up to the recording time to which is read at the previous time, and is not assigned with the scene number, as one group.

For example, in the case of FIG. 13, when the predetermined time period TH is assumed to be ten minutes, the time interval between the two pieces of adjacent operation log data is shorter than the predetermined time period TH from the first operation log data at the time "2013/2/1 10:00:15" through seven pieces of operation log data following the initial operation log data. However, a time difference between a time "2013/2/2 10:01:45" and a time "2013/2/1 10:12:00" is equal to or longer than ten minutes, and therefore, the control section 41 groups the operation log data from the time "2013/2/1 10:00:15" through the time "2013/2/1 10:01:45" and assigns the operation log data with a scene number, when the operation log data at the time "2013/2/1 10:12:00" is recorded. Here, the scene number is determined in such a manner that "1" is incremented by one. Therefore, the data including the operation log data-which is read first is assigned with the scene number "1", and the scene numbers which are assigned thereafter are incremented in sequence from "2".

Accordingly, the processing in S26 configures a grouping section that groups a plurality of operation log data which continue in time sequence, with the difference of the recording times of the two pieces of operation log data adjacent in time sequence is shorter than the predetermined time period TH, as one scene, when it is determined that the difference of the recording times of the two pieces of operation log data which are adjacent in time sequence has the time interval equal to or longer than the predetermined time period TH in S25. In particular, in S26, the scene number as the same scene identification information is assigned to the plurality of operation log data which are grouped as one scene.

Next, the control section 41 determines whether or not any operation log data to be read remains (S27). The operation log data extracted in S22 is read one by one, and when the last one is read, no operation log data to be read remains. Therefore, when no operation log data to be read remains (S27: YES), the processing is ended. If operation log data to be read remains, the processing returns to S23.

Further, when the time interval equal to or longer than the predetermined time period TH does not exist between the recording time tp1 of the operation log data read this time and the recording time to of the operation log data read at the previous time (S25: NO), the processing shifts to S27.

By the above processing being executed, the operation log data DDA shown in FIG. 13 can be grouped into each scene.

As above, according to the surgical system of the present embodiment, the medical support apparatus which can automatically perform setting of information such as on/off setting and change of the output set values of the respective apparatuses for each of the scenes of a surgical operation can be provided.

Note that in the aforementioned two embodiments, grouping of the operation log data is performed when the operation log data is collected, or grouping of the operation log data which is already collected and recorded is performed, but one scene may be enabled to be individually registered in the storage apparatus 42. That is to say, the set states and the output states of the respective apparatuses at present may be enabled to be registered in the storage apparatus 42 as one scene state, at an optional timing.

For example, when a predetermined scene registration button is displayed on the screen of the display device of the operation panel 21, and the predetermined scene registration button is pressed (namely, touched), the set states and the output states of the respective apparatuses at the time of the button being pressed are registered in the storage apparatus 42 as the operation log data of one scene.

The operation log data of the scene which is individually registered as above is added between optional scenes as the operation log data of one scene, into the operation log data according to the scene which is automatically created in the aforementioned first or second embodiment, or the operation log data of the scene which is individually registered as above is replaced with the information of setting of the scene or the like which is already registered, whereby addition and change of the scene is enabled.

As above, according to the surgical systems of the two embodiments described above, the medical support apparatus which can automatically perform setting of information such as on/off setting and change of the output set value of the respective apparatuses for each of the scenes of the surgical operation can be provided.

The present invention is not limited to the aforementioned embodiments, and various modifications, alterations and the like can be made within the range without departing from the gist of the present invention.

What is claimed is:

1. A medical support apparatus, comprising:
   a time interval determination section that determines whether or not a difference of recording times of two pieces of operation log data adjacent in time sequence has a time interval equal to or longer than a predetermined time period, with respect to the operation log data including identification information for identifying each of a surgical operator, a surgical operation and an apparatus to be controlled, operation contents for respective apparatuses to be controlled that are used at a time of the surgical operation, and a recording time; and
   a grouping section that groups a plurality of operation log data that continue in time sequence, with a difference of the recording times of the two pieces of operation log data adjacent in the time sequence being shorter than the predetermined time period, as one scene, when it is determined that the difference of the recording times of the two pieces of operation log data adjacent in time sequence has the time interval equal to or longer than the predetermined time period in the time interval determination section.

2. The medical support apparatus according to claim 1, wherein the time interval determination section determines whether or not the difference of the recording times of the two pieces of operation log data adjacent in time sequence has the time interval equal to or longer than the predetermined time period, when operation log data of operations to the respective apparatuses to be controlled that are performed during a surgical operation is stored in a storage apparatus.

3. The medical support apparatus according to claim 1, wherein the time interval determination section determines whether or not the difference of the recording times of the two pieces of operation log data adjacent in time sequence has the time interval equal to or longer than the predetermined time period, with respect to operation log data of operations to the respective apparatuses to be controlled that is stored in a storage apparatus.

4. The medical support apparatus according to claim 1, wherein the grouping section adds same scene identification information to the plurality of operation log data which are grouped as the one scene.

5. The medical support apparatus according to claim 1, further comprising:
a scene selection section that selects one scene from a plurality of scenes that are grouped by the grouping section; and
a scene operation signal outputting section that outputs operation signals to the respective apparatuses to be controlled, based on information of the apparatus to be controlled and the operation contents which are included in each of the plurality of operation log data with respect to the one scene selected in the scene selection section.

6. The medical support apparatus according to claim 5, further comprising:
an operation log data extraction section that extracts the operation log data corresponding to the identification information of the surgical operator and the surgical operation,
wherein the scene operation signal outputting section outputs the operation signals to the respective apparatuses to be controlled based on the information of the apparatus to be controlled and the operation contents which are included in the operation log data which is extracted by the operation log data extraction section.

7. The medical support apparatus according to claim 1, wherein the apparatus to be controlled is a teleconferencing system, and
the operation content includes teleconference connection information for establishing communication of the teleconferencing system with a teleconferencing system of a counterpart via a telephone line or a communication line.

8. The medical support apparatus according to claim 1, further comprising:
a recording section in which checklist information to be displayed on a display apparatus is recorded for each of the scenes.

9. An operation method of a medical support apparatus, comprising:
a time interval determination section of the medical support apparatus, which has operation log data including identification information for identifying each of a surgical operator, a surgical operation and an apparatus to be controlled, operation contents for respective apparatuses to be controlled that are used at a time of the surgical operation, and a recording time, determining whether or not a difference of recording times of two pieces of operation log data adjacent in time sequence has a time interval equal to or longer than a predetermined time period, with respect to the operation log data; and
a grouping section that groups the operation log data of the medical support apparatus grouping a plurality of operation log data that continue in time sequence, with a difference of the recording times of the two pieces of operation log data adjacent in time sequence being shorter than the predetermined time period, as one scene, when it is determined that the difference of the recording times of the two pieces of operation log data adjacent in time sequence has the time interval equal to or longer than the predetermined time period by the time interval determination section.

10. The operation method of a medical support apparatus according to claim 9,
wherein the time interval determination section determines whether or not the difference of the recording times of the two pieces of operation log data adjacent in time sequence has the time interval equal to or longer than the predetermined time period, when operation log data of operations to the respective apparatuses to be controlled that are performed during a surgical operation is stored in a storage apparatus.

11. The operation method of a medical support apparatus according to claim 9,
wherein the time interval determination section determines whether or not the difference of the recording times of the two pieces of operation log data adjacent in time sequence has the time interval equal to or longer than the predetermined time period, with respect to operation log data of operations to the respective apparatuses to be controlled that is stored in a storage apparatus.

12. The operation method of a medical support apparatus according to claim 9,
wherein the grouping section adds same scene identification information to the plurality of operation log data which are grouped as the one scene.

13. The operation method of a medical support apparatus according to claim 9,
wherein a scene selection section of the medical support apparatus selects one scene from a plurality of scenes that are grouped, and
a scene operation signal outputting section of the medical support apparatus outputs operation signals to the respective apparatuses to be controlled, based on information of the apparatus to be controlled and the operation contents which are included in each of the plurality of operation log data with respect to the one scene that is selected in the scene selection section.

14. The operation method of a medical support apparatus according to claim 13,
wherein an operation log data extraction section of the medical support apparatus extracts the operation log data corresponding to the identification information of the surgical operator and the surgical operation, and
the scene operation signal outputting section outputs the operation signals to the respective apparatuses to be controlled, based on the information of the apparatus to be controlled and the operation contents that are included in the operation log data which is extracted by the operation log data extraction section.

15. The operation method of a medical support apparatus according to claim 9,
   wherein the apparatus to be controlled is a teleconferencing system, and
   the operation content includes teleconference connection information for establishing communication of the teleconferencing system with a teleconferencing system of a counterpart via a telephone line or a communication line.

* * * * *